United States Patent
Olapade et al.

(10) Patent No.: US 11,630,233 B2
(45) Date of Patent: Apr. 18, 2023

(54) PREDICTING CONTAMINATION AND CLEAN FLUID PROPERTIES FROM DOWNHOLE AND WELLSITE GAS CHROMATOGRAMS

(71) Applicant: Halliburton Energy Services, Inc., Houston, TX (US)

(72) Inventors: Peter Ojo Olapade, Richmond, TX (US); Bin Dai, Spring, TX (US); Christopher Michael Jones, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 830 days.

(21) Appl. No.: 16/449,144

(22) Filed: Jun. 21, 2019

(65) Prior Publication Data
US 2020/0400858 A1    Dec. 24, 2020

(51) Int. Cl.
| | |
|---|---|
| *E21B 49/08* | (2006.01) |
| *G01V 9/00* | (2006.01) |
| *E21B 49/10* | (2006.01) |
| *G01N 30/86* | (2006.01) |
| *E21B 47/12* | (2012.01) |
| *E21B 17/10* | (2006.01) |

(52) U.S. Cl.
CPC .............. *G01V 9/00* (2013.01); *E21B 49/083* (2013.01); *E21B 49/10* (2013.01); *G01N 30/8651* (2013.01); *G01N 30/8675* (2013.01); *E21B 17/1078* (2013.01); *E21B 47/12* (2013.01); *E21B 49/0875* (2020.05)

(58) Field of Classification Search
CPC .... E21B 49/08; E21B 49/087; E21B 49/0875; E21B 49/088
See application file for complete search history.

(56) References Cited

U.S. PATENT DOCUMENTS

| | | | |
|---|---|---|---|
| 9,334,727 B2 | 5/2016 | Jones et al. | |
| 9,458,715 B2 | 10/2016 | van Hal et al. | |
| (Continued) | | | |

FOREIGN PATENT DOCUMENTS

WO    2018005695    1/2018

OTHER PUBLICATIONS

Schlumberger, MDT Modular Formation Dynamics Tester, SMP-5124, Jun. 2002.

(Continued)

*Primary Examiner* — Giovanna Wright
(74) *Attorney, Agent, or Firm* — John Wustenberg; C. Tumey Law Group PLLC (57) ABSTRACT

A method may comprise forming a data matrix, extracting chromatographs of a mud filtrate and a formation fluid, extracting concentration profiles of the mud filtrate and the formation fluid, and decomposing a data set on an information handling machine using a bilinear model. A system may comprise a downhole fluid sampling tool and an information handling tool. The downhole fluid sampling tool may comprise one or more multi-chamber sections, one or more fluid module sections, one or more gas chromatographers, wherein the one or more gas chromatographers are disposed in the one or more fluid module sections, and an information handling system.

21 Claims, 4 Drawing Sheets

(56) References Cited

U.S. PATENT DOCUMENTS

| | | | |
|---|---|---|---|
| 2008/0105032 A1* | 5/2008 | Reddy | E21B 49/08 |
| | | | 73/23.41 |
| 2013/0151159 A1 | 6/2013 | Pomerantz et al. | |
| 2015/0268374 A1 | 9/2015 | Rapoport | |
| 2016/0010453 A1* | 1/2016 | Breviere | E21B 49/086 |
| | | | 73/1.06 |
| 2016/0178599 A1* | 6/2016 | Gisolf | G01N 30/88 |
| | | | 73/23.35 |
| 2017/0321549 A1* | 11/2017 | Erdmann | E21B 49/086 |
| 2018/0094523 A1* | 4/2018 | van Hal | G01V 9/00 |

OTHER PUBLICATIONS

Baker Hughes, RCI and IFX Systems provide real-time fluid data and analysis in the North Sea, 2017.
Halliburton, Halliburton Reservoir Description Tool (RDT) Formation Tester, Formation Evaluation, H012350, Nov. 2016.
Halliburton, GeoTap IDS Fluid Identification and Sampling Sensor, Logging While Drilling, H013251, Jun. 2019.
International Search Report and Written Opinion for Application No. PCT/US2019/038602, dated Mar. 20, 2020.

* cited by examiner

PREDICTING CONTAMINATION AND CLEAN FLUID PROPERTIES FROM DOWNHOLE AND WELLSITE GAS CHROMATOGRAMS

BACKGROUND

During oil and gas exploration, many types of information may be collected and analyzed. The information may be used to determine the quantity and quality of hydrocarbons in a reservoir and to develop or modify strategies for hydrocarbon production. For instance, the information may be used for reservoir evaluation, flow assurance, reservoir stimulation, facility enhancement, production enhancement strategies, and reserve estimation. One technique for collecting relevant information involves obtaining and analyzing fluid samples from a reservoir of interest. There are a variety of different tools that may be used to obtain the fluid sample. The fluid sample may then be analyzed to determine fluid properties, including, without limitation, component concentrations, plus fraction molecular weight, gas-oil ratios, bubble point, dew point, phase envelope, viscosity, combinations thereof, or the like.

Due to overbalance pressure in a wellbore, drilling fluid invades the formation in the vicinity of the wellbore during drilling. Unlike water-based mud (WBM), oil-based mud (OBM) is miscible with the formation fluid and therefore changes the composition and the properties of the original formation fluid. For highly contaminated fluid, the measured composition and properties are not representative of the original formation fluid. Therefore, accurate composition and pressure, volume, and temperature (PVT) properties may characterize reservoir fluid and understanding architectural complexities of oil reservoirs. Understanding compartmentalization within reservoir and compositional grading with a compartment is essential to maximize oil recovery and these requires knowledge of clean formation fluid composition and properties are various depth in the reservoir.

Currently, methods and systems for reservoir architectural complexities include seismic survey and petrophysical logging tools. However, hydraulically sealing barriers may be quite thin and are often invisible to seismic response and high-resolution petrophysical measurements provide limited depth of investigation.

BRIEF DESCRIPTION OF THE DRAWINGS

These drawings illustrate certain aspects of some of the embodiments of the present disclosure, and should not be used to limit or define the disclosure.

DETAILED DESCRIPTION

Downhole sampling is a downhole operation that is used for formation evaluation, asset decisions, and operational decisions. As disclosed below, measurement operations of downhole fluid may be performed by a Gas Chromatography (GC) analyzer either at wellsite and/or downhole. It should be noted that while GC may be referred to within the document, GC includes all methods of chromatography. For example, liquid chromatography, thin layer chromatography, and/or the like. Included within chromatography is hyphenated chromatography such as any method of chromatography with mass spectroscopy, thermal conductivity detection, ultraviolet detection, and/or the like. Additionally, chromatography may be performed separately and augmented with other information that is independently formed from mass spectroscopy, microfluidic analysis, optical analysis, and/or the like. In some examples, devices providing chromatography like data defined as "differentiated compositional data" (i.e., compositional concentration as a function of molecular weight, or compositional concentration as a function of molecular size index, or compositional concentration as a function of vapor pressure) may be utilized. Additionally, the compositional concentration may be described against a functional change in component physical property. Such data may be generated by methods including but not limited to microfluidic analysis in combination with mass spectroscopy or membrane separation or mass balance or surface wave acoustic analysis. For wellsite with a GC, samples from different depth in addition to the filtrate sample may be analyzed together on site. Similarly, for downhole GC, samples at different pumpout volume at the same depth or different depth may be analyzed together. Analysis of the pumpout may provide mud filtrate contamination level, clean fluid composition, and fluid properties. The clean fluid composition and properties may be used for continuity assessment or augmentation of fluid data when used in comparison with downhole samples. Furthermore, reservoir architecture including parameters such as compositional grading, and compartmentalization may be determined. The compositional parameters determined may be used in reservoir simulation.

Figure 1:
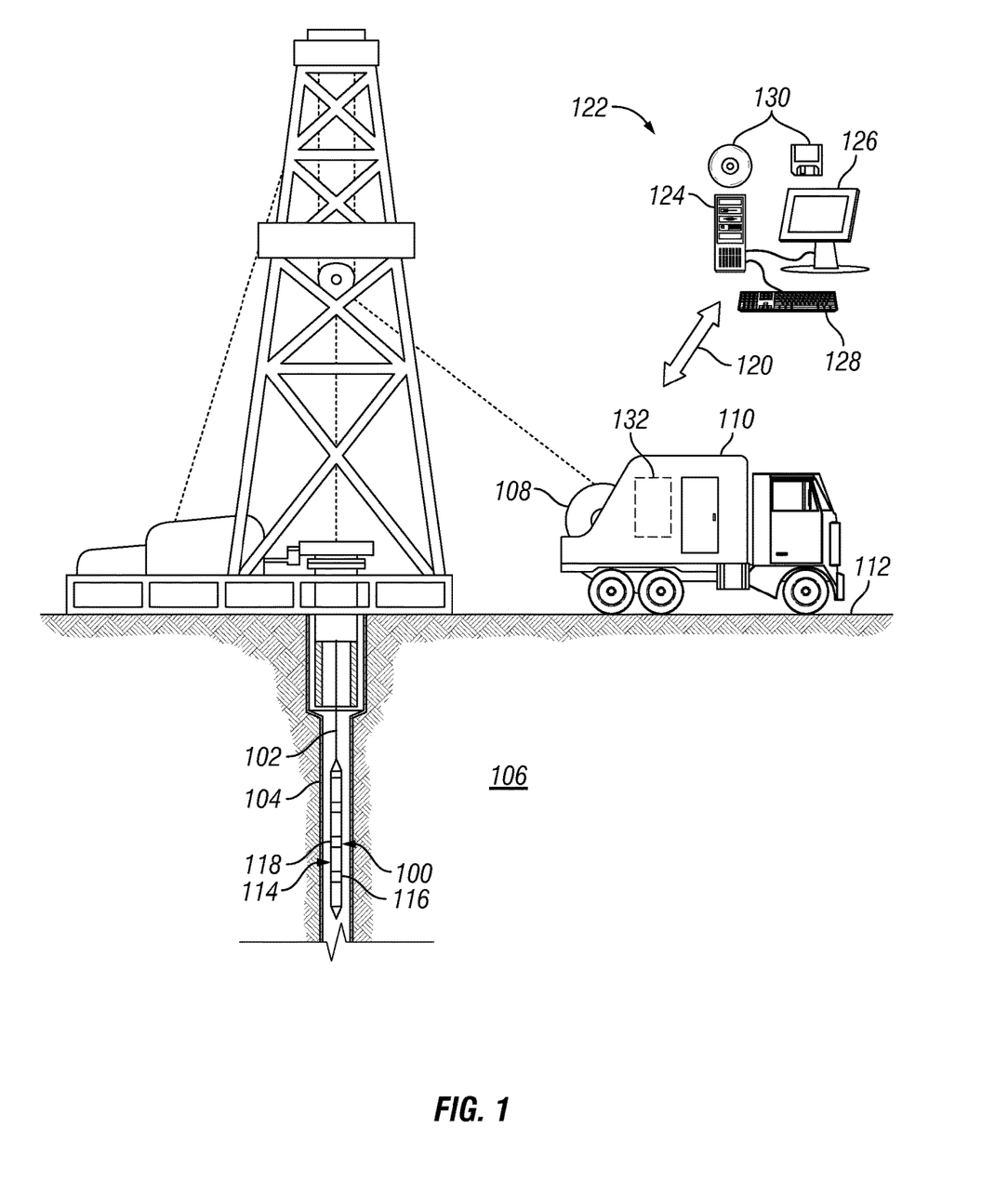
FIG. 1 is a schematic diagram of an example downhole fluid sampling tool on a wireline.

FIG. 1 is a schematic diagram is shown of downhole fluid sampling tool 100 on a conveyance 102. As illustrated, wellbore 104 may extend through subterranean formation 106. In examples, reservoir fluid may be contaminated with well fluid (e.g., drilling fluid) from wellbore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 1 shows a vertical or low inclination angle well, high inclination angle or horizontal placement of the well and equipment is also possible. It should further be noted that while FIG. 1 generally depicts a land-based operation, those skilled in the art will readily recognize that the principles described herein are equally applicable to subsea operations that employ floating or sea-based platforms and rigs, without departing from the scope of the disclosure.

As illustrated, a hoist 108 may be used to run downhole fluid sampling tool 100 into wellbore 104. Hoist 108 may be disposed on a vehicle 110. Hoist 108 may be used, for example, to raise and lower conveyance 102 in wellbore 104. While hoist 108 is shown on vehicle 110, it should be understood that conveyance 102 may alternatively be disposed from a hoist 108 that is installed at surface 112 instead of being located on vehicle 110. Downhole fluid sampling tool 100 may be suspended in wellbore 104 on conveyance 102. Other conveyance types may be used for conveying downhole fluid sampling tool 100 into wellbore 104, including coiled tubing and wired drill pipe, for example. Downhole fluid sampling tool 100 may include a tool body 114, which may be elongated as shown on FIG. 1. Tool body 114 may be any suitable material, including without limitation titanium, stainless steel, alloys, plastic, combinations thereof, and the like. Downhole fluid sampling tool 100 may further include one or more sensors 116 for measuring properties of the fluid sample, reservoir fluid, wellbore 104, subterranean formation 106, or the like. In examples, downhole fluid sampling tool 100 may also include a fluid analysis module 118, which may be operable to process information regarding fluid sample, as described below. Downhole fluid sampling tool 100 may be used to collect fluid samples from subterranean formation 106 and may obtain and separately store different fluid samples from subterranean formation 106.

In examples, fluid analysis module 118 may include at least one a sensor that may continuously monitor a reservoir fluid. Such sensors include optical sensors, acoustic sensors, electromagnetic sensors, conductivity sensors, resistivity sensors, selective electrodes, density sensors, mass sensors, thermal sensors, chromatography sensors, viscosity sensors, bubble point sensors, fluid compressibility sensors, flow rate sensors. Sensors may measure a contrast between drilling fluid filtrate properties and formation fluid properties.

In examples, fluid analysis module 118 may be a gas chromatography analyzer (GC). A gas chromatography analyzer may separate and analyze compounds that may be vaporized without decomposition. Fluid samples from wellbore 104 may be injected into a GC column and vaporized. Different compounds may be separated due to their retention time difference in the vapor state. Analyses of the compounds may be displayed in GC chromatographs. In examples, a mixture of formation fluid and drilling fluid filtrate may be separated and analyzed to determine the properties within the formation fluid and drilling fluid filtrate.

Fluid analysis module 118 may be operable to derive properties and characterize the fluid sample. By way of example, fluid analysis module 118 may measure absorption, transmittance, or reflectance spectra and translate such measurements into component concentrations of the fluid sample, which may be lumped component concentrations, as described above. The fluid analysis module 118 may also measure gas-to-oil ratio, fluid composition, water cut, live fluid density, live fluid viscosity, formation pressure, and formation temperature. Fluid analysis module 118 may also be operable to determine fluid contamination of the fluid sample and may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, fluid analysis module 118 may include random access memory (RAM), one or more processing units, such as a central processing unit (CPU), or hardware or software control logic, ROM, and/or other types of nonvolatile memory.

Any suitable technique may be used for transmitting signals from the downhole fluid sampling tool 100 to surface 112. As illustrated, a communication link 120 (which may be wired or wireless, for example) may be provided that may transmit data from downhole fluid sampling tool 100 to an information handling system 122 at surface 112. Information handling system 122 may include a processing unit 124, a monitor 126, an input device 128 (e.g., keyboard, mouse, etc.), and/or computer media 130 (e.g., optical disks, magnetic disks) that can store code representative of the methods described herein. Information handling system 122 may act as a data acquisition system and possibly a data processing system that analyzes information from downhole fluid sampling tool 100. For example, information handling system 122 may process the information from downhole fluid sampling tool 100 for determination of fluid contamination. Information handling system 122 may also determine additional properties of the fluid sample (or reservoir fluid), such as component concentrations, pressure-volume-temperature properties (e.g., bubble point, phase envelop prediction, etc.) based on the fluid characterization. This processing may occur at surface 112 in real-time. Alternatively, the processing may occur downhole hole or at surface 112 or another location after recovery of downhole fluid sampling tool 100 from wellbore 104. Alternatively, the processing may be performed by an information handling system in wellbore 104, such as fluid analysis module 118. The resultant fluid contamination and fluid properties may then be transmitted to surface 112, for example, in real-time.

It should be noted that in examples a gas chromatographer 132 may be disposed on surface 112 and analyze samples captures by downhole fluid sampling tool 100. For example, fluid analysis module 118 may capture fluid samples and bring them to the surface 112 for analysis at the wellsite. As illustrated, gas chromatographer 132 may be disposed in vehicle 110. However, gas chromatographer 132 may be a standalone assembly that may be available at the wellsite. Additionally, information handling system 122 may be connected to gas chromatographer 132 through communication link 120. In examples, gas chromatographer 132 may operate and function as described above.

Figure 2:
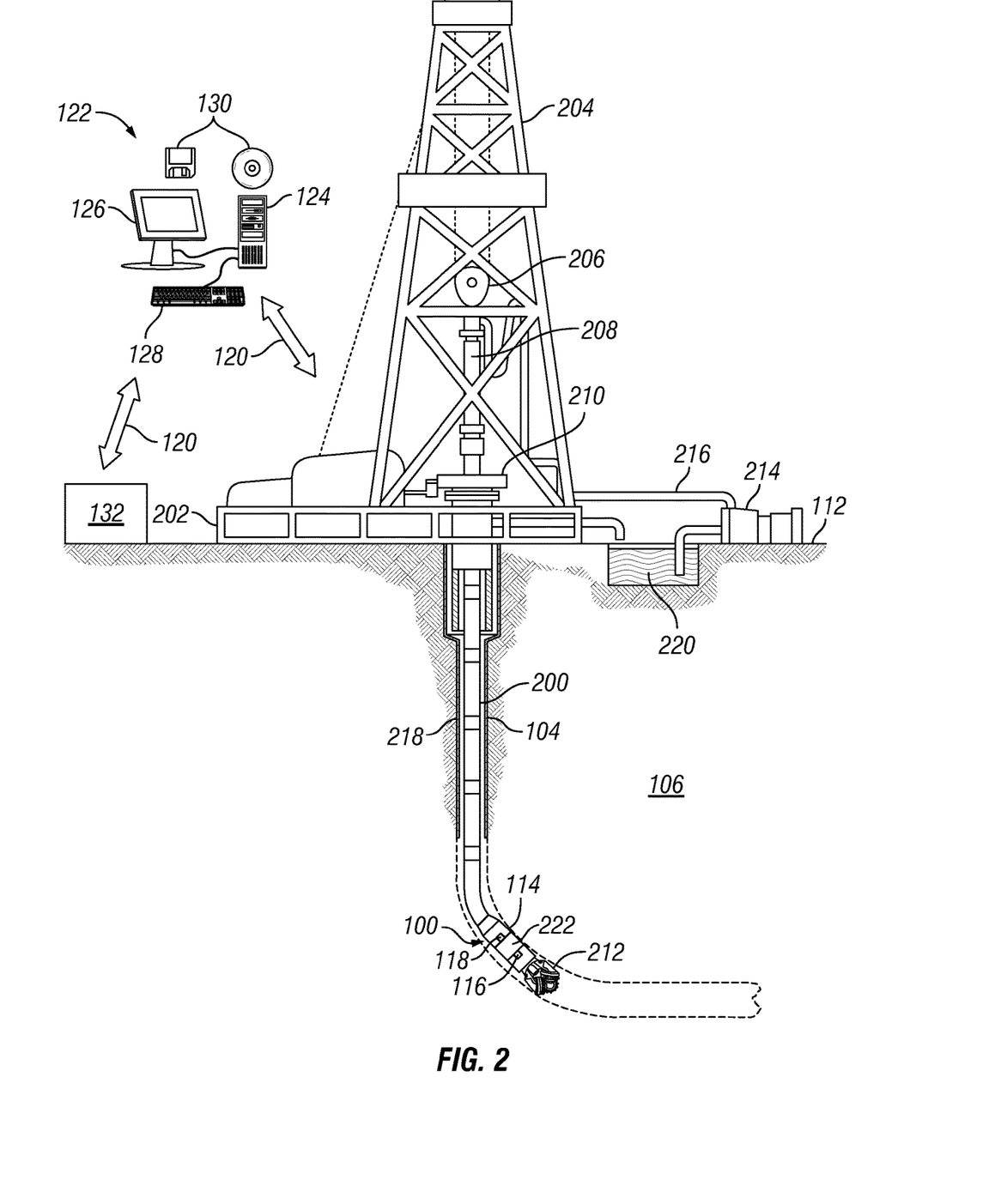
FIG. 2 is a schematic diagram of an example downhole fluid sampling tool on a drill string.

Referring now to FIG. 2, FIG. 2 is a schematic diagram is shown of downhole fluid sampling tool 100 disposed on a drill string 200 in a drilling operation. Downhole fluid sampling tool 100 may be used to obtain a fluid sample, for example, a fluid sample of a reservoir fluid from subterranean formation 106. The reservoir fluid may be contaminated with well fluid (e.g., drilling fluid) from wellbore 104. As described herein, the fluid sample may be analyzed to determine fluid contamination and other fluid properties of the reservoir fluid. As illustrated, a wellbore 104 may extend through subterranean formation 106. While the wellbore 104 is shown extending generally vertically into the subterranean formation 106, the principles described herein are also applicable to wellbores that extend at an angle through the subterranean formation 106, such as horizontal and slanted wellbores. For example, although FIG. 2 shows a vertical or low inclination angle well, high inclination angle or horizontal placement of the well and equipment is also possible. It should further be noted that while FIG. 2 generally depicts a land-based operation, those skilled in the art will readily recognize that the principles described herein are equally applicable to subsea operations that employ floating or sea-based platforms and rigs, without departing from the scope of the disclosure.

As illustrated, a drilling platform 202 may support a derrick 204 having a traveling block 206 for raising and lowering drill string 200. Drill string 200 may include, but is not limited to, drill pipe and coiled tubing, as generally known to those skilled in the art. A kelly 208 may support drill string 200 as it may be lowered through a rotary table 210. A drill bit 212 may be attached to the distal end of drill string 200 and may be driven either by a downhole motor and/or via rotation of drill string 200 from the surface 112. Without limitation, drill bit 212 may include, roller cone bits, PDC bits, natural diamond bits, any hole openers, reamers, coring bits, and the like. As drill bit 212 rotates, it may create and extend wellbore 104 that penetrates various subterranean formations 106. A pump 214 may circulate drilling fluid through a feed pipe 216 to kelly 208, downhole through interior of drill string 200, through orifices in drill bit 212, back to surface 112 via annulus 218 surrounding drill string 200, and into a retention pit 220.

Drill bit 212 may be just one piece of a downhole assembly that may include one or more drill collars 222 and downhole fluid sampling tool 100. Downhole fluid sampling tool 100, which may be built into the drill collars 22) may gather measurements and fluid samples as described herein. One or more of the drill collars 222 may form a tool body 114, which may be elongated as shown on FIG. 2. Tool body 114 may be any suitable material, including without limitation titanium, stainless steel, alloys, plastic, combinations thereof, and the like. Downhole fluid sampling tool 100 may be similar in configuration and operation to downhole fluid sampling tool 100 shown on FIG. 1 except that FIG. 2 shows downhole fluid sampling tool 100 disposed on drill string 200. Alternatively, the sampling tool may be lowered into the wellbore after drilling operations on a wireline.

Downhole fluid sampling tool 100 may further include one or more sensors 116 for measuring properties of the fluid sample reservoir fluid, wellbore 104, subterranean formation 106, or the like. The properties of the fluid are measured as the fluid passes from the formation through the tool and into either the wellbore or a sample container. As fluid is flushed in the near wellbore region by the mechanical pump, the fluid that passes through the tool generally reduces in drilling fluid filtrate content, and generally increases in formation fluid content. The downhole fluid sampling tool 100 may be used to collect a fluid sample from subterranean formation 106 when the filtrate content has been determined to be sufficiently low. Sufficiently low depends on the purpose of sampling. For some laboratory testing below 10% drilling fluid contamination is sufficiently low, and for other testing below 1% drilling fluid filtrate contamination is sufficiently low. Sufficiently low also depends on the nature of the formation fluid such that lower requirements are generally needed, the lighter the oil as designated with either a higher GOR or a higher API gravity. Sufficiently low also depends on the rate of cleanup in a cost benefit analysis since longer pumpout times required to incrementally reduce the contamination levels may have prohibitively large costs. As previously described, the fluid sample may include a reservoir fluid, which may be contaminated with a drilling fluid or drilling fluid filtrate. Downhole fluid sampling tool 100 may obtain and separately store different fluid samples from subterranean formation 106 with fluid analysis module 118. Fluid analysis module 118 may operate and function in the same manner as described above. However, storing of the fluid samples in the downhole fluid sampling tool 100 may be based on the determination of the fluid contamination. For example, if the fluid contamination exceeds a tolerance, then the fluid sample may not be stored. If the fluid contamination is within a tolerance, then the fluid sample may be stored in the downhole fluid sampling tool 100.

As previously described, information from downhole fluid sampling tool 100 may be transmitted to an information handling system 122, which may be located at surface 112. As illustrated, communication link 120 (which may be wired or wireless, for example) may be provided that may transmit data from downhole fluid sampling tool 100 to an information handling system 111 at surface 112. Information handling system 140 may include a processing unit 124, a monitor 126, an input device 128 (e.g., keyboard, mouse, etc.), and/or computer media 130 (e.g., optical disks, magnetic disks) that may store code representative of the methods described herein. In addition to, or in place of processing at surface 112, processing may occur downhole (e.g., fluid analysis module 118). In examples, information handling system 122 may perform computations to estimate clean fluid composition.

As previously described above, a gas chromatographer 132 may be disposed on surface 112 and analyze samples captures by downhole fluid sampling tool 100. For example, fluid analysis module 118 may capture fluid samples and bring them to the surface 112 for analysis at the wellsite. As illustrated, gas chromatographer 132 may be a standalone assembly that may be available at the wellsite. Additionally, information handling system 122 may be connected to gas chromatographer 132 through communication link 120. In examples, gas chromatographer 132 may operate and function as described above.

Figure 3:
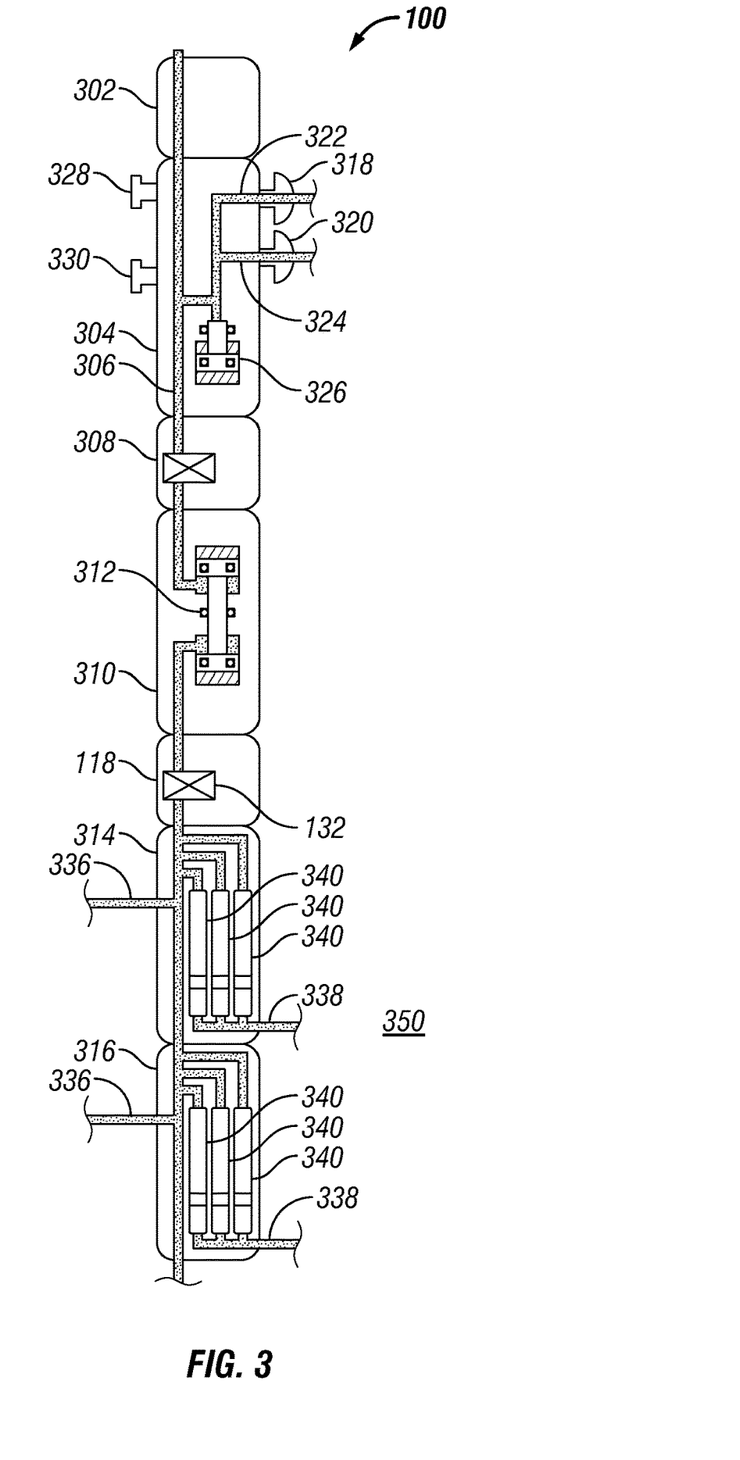
FIG. 3 is a schematic diagram of a downhole fluid sampling tool with a filter disposed in a chamber.

FIG. 3 is a schematic of downhole fluid sampling tool 100. In examples, downhole fluid sampling tool 100 includes a power telemetry section 302 through which the tool communicates with other actuators and sensors 116 in drill string 200 or conveyance 102 (e.g., referring to FIGS. 1 and 2), and/or directly with a surface telemetry system (not illustrated). In examples, power telemetry section 302 may also be a port through which the various actuators (e.g. valves) and sensors (e.g., temperature and pressure sensors) in the downhole fluid sampling tool 100 may be controlled and monitored. In examples, power telemetry section 302 includes a computer that exercises the control and monitoring function. In one embodiment, the control and monitoring function is performed by a computer in another part of the drill string or wireline tool (not shown) or by information handling system 122 on surface 112 (e.g., referring to FIGS. 1 and 2).

In examples, downhole fluid sampling tool 100 includes a dual probe section 304, which extracts fluid from the reservoir and delivers it to a channel 306 that extends from one end of downhole fluid sampling tool 100 to the other. Without limitation, dual probe section 304 includes two probes 318, 320 which may extend from downhole fluid sampling tool 100 and press against the inner wall of wellbore 104 (e.g., referring to FIG. 1). Probe channels 322, 324 may connect probes 318, 320 to channel 306. The high-volume bidirectional pump 312 may be used to pump fluids from the reservoir, through probe channels 322, 324 and to channel 306. Alternatively, a low volume pump 326 may be used for this purpose. Two standoffs or stabilizers 328, 330 hold downhole fluid sampling tool 100 in place as probes 318, 320 press against the wall of wellbore 104. In examples, probes 318, 320 and stabilizers 328, 330 may be retracted when downhole fluid sampling tool 100 may be in motion and probes 318, 320 and stabilizers 328, 330 may be extended to sample the formation fluids at any suitable location in wellbore 104. Other probe sections include focused sampling probes, oval probes, or packers.

In examples, channel 306 may be connected to other tools disposed on drill string 200 or conveyance 102 (e.g., referring to FIGS. 1 and 2). In examples, downhole fluid sampling tool 100 may also include a quartz gauge section 308, which may include sensors to allow measurement of properties, such as temperature and pressure, of fluid in channel 306. Additionally, downhole fluid sampling tool 100 may include a flow-control pump-out section 310, which may include a high-volume bidirectional pump 312 for pumping fluid through channel 306. In examples, downhole fluid sampling tool 100 may include two multi-chamber sections 314, 316, referred to collectively as multi-chamber sections 314, 316 or individually as first multi-chamber section 314 and second multi-chamber section 316, respectively.

In examples, multi-chamber sections 314, 316 may be separated from flow-control pump-out section 310 by fluid analysis module 118, which may house at least one sensor, for example gas chromatographer 132. Gas chromatographer 132 may be displaced within fluid analysis module 118 in-line with channel 306 to be a "flow through" sensor. In alternate examples, gas chromatographer 132 may be connected to channel 306 via an offshoot of channel 306. Without limitation, fluid analysis module 118 may also include optical sensors, acoustic sensors, electromagnetic sensors, conductivity sensors, resistivity sensors, selective electrodes, density sensors, mass sensors, thermal sensors, chromatography sensors, viscosity sensors, bubble point sensors, fluid compressibility sensors, flow rate sensors, microfluidic sensors, selective electrodes such as ion selective electrodes, and/or combinations thereof. In examples, gas chromatographer 132 may operate and/or function as described above.

Additionally, multi-chamber section 314, 316 may include access channel 336 and chamber access channel 338. Without limitation, access channel 336 and chamber access channel 338 may operate and function to either allow a solids-containing fluid (e.g., mud) disposed in wellbore 104 in or provide a path for removing fluid from downhole fluid sampling tool 100 into wellbore 104. As illustrated, multi-chamber section 314, 316 may include a plurality of chambers 340. Chambers 340 may be sampling chamber that may be used to sample wellbore fluids, formation fluids, and/or the like during measurement operations.

As discussed above, gas chromatographer 132 may use methods of gas chromatography (GC) at a wellsite or downhole to analyze mud filtrate and different samples. At the wellsite, in addition to analyzing the mud filtrate sample, samples at different depth may be analyzed using GC. Assumption that the formation fluid at different depth may be similar and that mud filtrate each of the depths may be similar is made. Chromatograms of mud filtrates and that of samples at different depth combined together as data matrix and the contamination is treated as a mixing problem of formation fluid and mud filtrate. Methods such as multivariate curve resolution (MCR) may be used to estimate the concentrate and spectra of formation fluid and mud filtrate. The concentration of the mud filtrate gives the contamination level of each sample and clean fluid composition may be estimated from the spectra data of formation fluid. Described herein, MCR is an endmember deconvolution technique, and use of the MCR will refer to any endmember deconvolution technique. Other endmember deconvolution techniques that MCR will refer to include but are not limited to factor analysis, wavelet analysis, principal component analysis, and other linear or nonlinear pattern recognition techniques.

Similarly, for downhole GC, multiple samples during pumpout at the same depth are analyzed using GC. It is assumed that mud filtrate at different pumping volume may be the same and fluid composition may also be the same. The chromatogram at different pumpout volume at combined to form the data matrix and the problem is treated as a mixing problem of formation fluid and mud filtrate. The concentration of the mud filtrate gives the contamination level of each sample and clean fluid composition may be estimated from the spectra data of the formation fluid.

Figure 4:
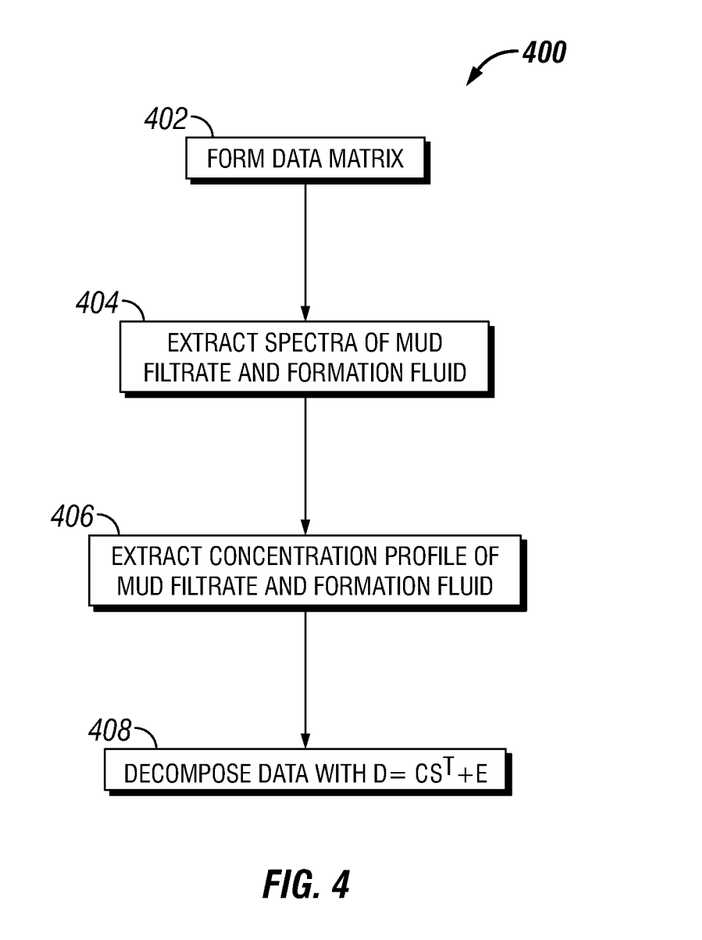
FIG. 4 illustrates a workflow to analyze mud filtrate and different sample taken downhole.

FIG. 4 illustrates workflow 400 to analyze mud filtrate and different sample taken downhole. Workflow 400 may begin with step 402 to form a data matrix. The data matrix may include the chromatograms from mud filtrate and from different samples where from different depth, samples obtained when downhole fluid sampling tool 100 (e.g., referring to FIG. 1) is brought to the surface or from the sample depth taking at different pumping volume during the pumpout for downhole GC application. Samples taken downhole may include two components (mud filtrate and formation fluid) coexisting in each chromatogram. In step 404 one or more chromatographs may be formed from an extracted spectra of mud filtrate and formation fluid. This step may include using a Multivariate Curve Resolution (MCR) to extract the pure spectra of each of the components coexisting in the samples. An MCR is a method for resolving mixtures by determining the number of constituents, their response profiles and their estimated concentrations, when no prior information is available about the nature and composition of these mixtures. In step 406 an operator may extract a concentration profile of the mud filtrate and formation fluid. This step may include using an MCR to extract the concentration profiles of each component. In step 408 an operator may use an information handling machine 122 (e.g., referring to FIG. 1) to decompose data according to a bilinear model, $D=CS^T+E$, Where D—Data matrix, C—resolved concentration profiles, S—resolved spectra profiles, T is the transpose of matrix S, and E—is the error in the estimation.

Using workflow 400 may improve estimation of the clean fluid compositions: methane (C1), ethane (C2), propane (C3), butane (C4) and pentane (C5) hexane C6 and heptane plus (C7+) using GC data and MCR method. As discussed above improvements may allow for using clean fluid composition and equation of state to estimate physical and/or chemical properties including fluid density, bubble point and gas to oil ratio (GOR) at downhole condition in real time. Improvements from workflow 400 may also allow for the use of clean fluid chemical and/or physical properties from GC data/MCR data to guide subsequent wireline or LWD sampling or pressure testing operations. Additional improvements may use clean fluid compositions at different depths to determine compartmentalization and compositional gradient within a compartment.

Compartmentalization is defined as identifying and producing different hydrocarbon deposits within a subterranean environment. In examples, there may be a single hydrocarbon deposit or multiple hydrocarbon deposits within a compartment. A compartment is defined as a geographic area over which hydrocarbons may be obtained. For example, two separate compartments may be produced hydrocarbons separately as the subterranean environment may not allow for fluid flow between each compartment. However, in some subterranean environments different hydrocarbon deposits may be fluidly connected. Therefore, if one deposit is drained than the second deposit with drain as well. Both deposits would be grouped into a single compartment because as one deposit is drained fluid, fluid within both deposits will drain.

Fluid within each compartment, each deposit, may have variations. Fluid variations may be monitored and graded as a compositional gradient as a function of depth. Compositional grading may be found using equation of state models. To determine compositional grading, properties of formation fluid are found, as discussed above, by determining the amount of fluid filtrate within the formation fluid. After determining properties of the formation fluid, an MCR algorithm may use the properties with an equation of state to determine compositional grade. Other methods may be utilized to determine compositional grade, such as exponential models for growth or decline may be used.

When determining compositional grading, if a model such as an equation of state model, physical model, or an empirical model does not fit characteristics of the hydrocarbon deposit, it may be assumed that the hydrocarbon deposit may include two or more separate compartments. Fluid dynamics may be used to determine different hydrocarbon deposits. For example, a higher density fluid will not be disposed on a lower density fluid and a lower GOR fluid will not be on a higher GOR fluid. Fluid dynamics may indicate separate hydrocarbon deposits without using a trend model.

Equation of state model, discussed above, may generally be physical models that may be cubic equation of state models. Examples of cubic equation of state models may be a Peng-Robinson, SRK, and/or the like. Additionally, equation state models may be non-cubic equation of state models such as, PC-SAFT, polymer equation of state, and/or the like. Each equation of state model may be used to measure at least a portion of the fluid such as asphaltene variation. Equation of state models may utilize physics in understanding reservoir characteristics such as temperature, pressure, and composition. While empirical models are good at testing for continuity, they may fit to discontinuous fluid systems, which may provide false positives.

The preceding description provides various embodiments of systems and methods of use which may contain different method steps and alternative combinations of components. It should be understood that, although individual embodiments may be discussed herein, the present disclosure covers all combinations of the disclosed embodiments, including, without limitation, the different component combinations, method step combinations, and properties of the system.

Statement 1. A method may comprise forming a data matrix; extracting chromatographs of a mud filtrate and a formation fluid; extracting concentration profiles of the mud filtrate and the formation fluid; and decomposing a data set on an information handling machine using a bilinear model.

Statement 2. The method of statement 1, wherein the bilinear model is $D=CS^T+E$, wherein D is the data matrix, C is the concentration profiles of the mud filtrate and the formation fluid, S is chromatographs of the mud filtrate and the formation fluid, T is a transpose of matrix S, and E is error.

Statement 3. The method of statement 1 or 2, further comprising using multivariate curve resolution for the extracting chromatographs of the mud filtrate and the formation fluid.

Statement 4. The method of statements 1-3, further comprising using a multivariate curve resolution for extracting a concentration profile of the mud filtrate and the formation fluid.

Statement 5. The method of statements 1-4, wherein the data matrix comprises of one or more chromatograms from the mud filtrate or the formation fluid.

Statement 6. The method of statements 1-5, further comprising performing the extracting chromatographs and the extracting concentration profiles at a well site or in a downhole fluid sampling tool.

Statement 7. A method may comprise disposing a downhole fluid sampling tool into a wellbore at a first location, wherein the downhole fluid sampling tool comprises: at least one multi-chamber section; at least one fluid module section; and activating a pump to draw a solids-containing fluid disposed in the wellbore into the downhole fluid sampling tool; raising the downhole fluid sampling tool to surface; disposing the solids-containing fluid into a gas chromatographer; measuring the drilling fluid filtrate from the solids-containing fluid with the gas chromatographer to form data; inputting the data into an information handling system; forming a data matrix from the data; extracting chromatographs of a mud filtrate and formation fluid from the solids-containing fluid; extracting a concentration profile of the mud filtrate and the formation fluid; and decomposing a data set on an information handling machine using a bilinear model.

Statement 8. The method of statement 7, wherein the bilinear model is $D=CS^T+E$, wherein D is the data matrix, C is the concentration profile of the mud filtrate and the formation fluid, S is the chromatographs of the mud filtrate and the formation fluid, T is a transpose of matrix S, and E is error.

Statement 9. The method of statements 7 or 8, further comprising using multivariate curve resolution for the extracting a spectra or a concentration profile of a mud filtrate and formation fluid.

Statement 10. The method of statements 7-9, wherein the data matrix comprises of one or more chromatograms from the mud filtrate or the formation fluid.

Statement 11. The method of statements 7-10, further comprising performing the extracting chromatographs and the extracting concentration profiles in the downhole fluid sampling tool.

Statement 12. A system may comprise a downhole fluid sampling tool comprising: one or more multi-chamber sections; one or more fluid module sections; one or more gas chromatographers, wherein the one or more gas chromatographers are disposed in the one or more fluid module sections; and an information handling system configured to: form a data matrix; extract chromatographs of a mud filtrate and a formation fluid from the downhole fluid sampling tool; extract a concentration profile of the mud filtrate and the formation fluid from the downhole fluid sampling tool; and decompose a data set with, $D=CS^T+E$, wherein D is the data matrix, C is the concentration profile of the mud filtrate and the formation fluid, S is the chromatographs of the mud filtrate and the formation fluid, T is a transpose of matrix S, and E is error.

Statement 13. The system of statement 12, wherein the information handling system is further configured to use multivariate curve resolution for the extracting chromatograph profiles of a mud filtrate and the formation fluid.

Statement 14. The system of statements 12 or 13, wherein the information handling system is further configured to use multivariate curve resolution for extracting a concentration profile of the mud filtrate and the formation fluid.

Statement 15. The system of statements 12-14, wherein the data matrix comprises of one or more chromatograms from the mud filtrate or the formation fluid.

Statement 16. The system of statements 12-15, wherein the downhole fluid sampling tool further comprises one or more probes.

Statement 17. The system of statements 12-16, wherein the downhole fluid sampling tool further comprises one or more stabilizers.

Statement 18. The system of statements 12-17, wherein the downhole fluid sampling tool is connected to a conveyance.

Statement 19. The system of statements 12-18, wherein the downhole fluid sampling tool is connected to a drill string.

Statement 20. The system of statements 12-19, wherein the downhole fluid sampling tool further comprises a pump, wherein the pump is configured to draw a solids-containing fluid into the one or more fluid module sections.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

Therefore, the present embodiments are well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Although individual embodiments are discussed, the disclosure covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present disclosure. If there is any conflict in the usages of a word or term in this specification and one or more patent(s) or other documents that may be incorporated herein by reference, the definitions that are consistent with this specification should be adopted.

What is claimed is:

1. A method comprising:
   collecting at least a first sample and a second sample from a downhole fluid with a downhole fluid sampling tool;
   measuring the first sample and the second sample in a chromatograph to form a first chromatogram from the first sample and a second chromatogram from the second sample;
   forming a data matrix, wherein the data matrix comprises the first chromatogram and the second chromatogram;
   extracting the first chromatogram and the second chromatogram, wherein the first chromatogram is from a mud filtrate and the second chromatogram is from a formation fluid;
   extracting concentration profiles of the mud filtrate and the formation fluid; and
   decomposing a data set on an information handling machine using a bilinear model.

2. The method of claim 1, wherein the bilinear model is $D=CS^T+E$, wherein D is the data matrix, C is the concentration profiles of the mud filtrate and the formation fluid, S is chromatographs of the mud filtrate and the formation fluid, T is a transpose of matrix S, and E is error.

3. The method of claim 1, further comprising using multivariate curve resolution for the extracting chromatographs of the mud filtrate and the formation fluid or the extracting the concentration profile of the mud filtrate and the formation fluid.

4. The method of claim 1, further comprising compartmentalizing a formation into one or more compartments based at least in part on the concentration profiles and identifying a compositional gradient for each of the one or more compartments.

5. The method of claim 1, further comprising guiding a sampling operation or a pressure testing operation based at least in part on the concentration profiles.

6. The method of claim 1, further comprising performing the extracting chromatographs and the extracting concentration profiles at a well site or in a downhole fluid sampling tool.

7. A method comprising:
   disposing a downhole fluid sampling tool into a wellbore at a first location, wherein the downhole fluid sampling tool comprises:
      at least one multi-chamber section;
      at least one fluid module section; and
   activating a pump to draw a solids-containing fluid disposed in the wellbore into the downhole fluid sampling tool;
   raising the downhole fluid sampling tool to surface;
   disposing the solids-containing fluid into a gas chromatograph;
   measuring the drilling fluid filtrate from the solids-containing fluid with the gas chromatograph to form data, wherein the data comprises chromatograms from each of two or more samples, wherein the two or more samples comprise a mud filtrate and a formation fluid;
   inputting the data into an information handling system;
   forming a data matrix from the data;
   extracting chromatographs of flail the mud filtrate and the formation fluid from the solids-containing fluid;
   extracting a concentration profile of the mud filtrate and the formation fluid; and
   decomposing a data set on an information handling machine using a bilinear model.

8. The method of claim 7, wherein the bilinear model is $D=CS^T+E$, wherein D is the data matrix, C is the concentration profile of the mud filtrate and the formation fluid, S is the chromatographs of the mud filtrate and the formation fluid, T is a transpose of matrix S, and E is error.

9. The method of claim 7, further comprising using multivariate curve resolution for the extracting a spectra or a concentration profile of a mud filtrate and formation fluid.

10. The method of claim 7, further comprising performing the extracting chromatographs and the extracting concentration profiles in the downhole fluid sampling tool.

11. The method of claim 7, further comprising compartmentalizing a formation into one or more compartments based at least in part on the concentration profiles and identifying a compositional gradient for each of the one or more compartments.

12. A system comprising:
   a downhole fluid sampling tool comprising:
      one or more multi-chamber sections;
      one or more fluid module sections;
      one or more gas chromatographs, wherein the one or more gas chromatographs are disposed in the one or more fluid module sections; and
   an information handling system configured to:
      form a data matrix;
      extract chromatographs of a mud filtrate and a formation fluid from the downhole fluid sampling tool;
      extract a concentration profile of the mud filtrate and the formation fluid from the downhole fluid sampling tool; and
      decompose a data set with, $D=CS^T+E$, wherein D is the data matrix, C is the concentration profile of the mud filtrate and the formation fluid, S is the chromatographs of the mud filtrate and the formation fluid, T is a transpose of matrix S, and E is error.

13. The system of claim 12, wherein the information handling system is further configured to use multivariate curve resolution for the extracting chromatograph profiles of a mud filtrate and the formation fluid.

14. The system of claim 12, wherein the information handling system is further configured to use multivariate curve resolution for extracting a concentration profile of the mud filtrate and the formation fluid.

15. The system of claim 12, wherein the data matrix comprises of one or more chromatograms from the mud filtrate or the formation fluid.

16. The system of claim 12, wherein the downhole fluid sampling tool further comprises one or more probes.

17. The system of claim 12, wherein the downhole fluid sampling tool further comprises one or more stabilizers.

18. The system of claim 12, wherein the downhole fluid sampling tool is connected to a conveyance.

19. The system of claim 12, wherein the downhole fluid sampling tool is connected to a drill string.

20. The system of claim 12, wherein the downhole fluid sampling tool further comprises a pump, wherein the pump is configured to draw a solids-containing fluid into the one or more fluid module sections.

21. A method comprising:
disposing a downhole fluid sampling tool into a wellbore at a first location, wherein the downhole fluid sampling tool comprises:
at least one multi-chamber section;
at least one fluid module section; and
activating a pump to draw a solids-containing fluid disposed in the wellbore into the downhole fluid sampling tool;
raising the downhole fluid sampling tool to surface;
disposing the solids-containing fluid into a gas chromatograph;
measuring the drilling fluid filtrate from the solids-containing fluid with the gas chromatograph to form data;
inputting the data into an information handling system;
forming a data matrix from the data;
extracting chromatographs of a mud filtrate and formation fluid from the solids-containing fluid;
extracting a concentration profile of the mud filtrate and the formation fluid; and
decomposing a data set on an information handling machine using a bilinear model wherein the bilinear model is $D=CS^T+E$, wherein D is the data matrix, C is the concentration profile of the mud filtrate and the formation fluid, S is the chromatographs of the mud filtrate and the formation fluid, T is a transpose of matrix S, and E is error.

* * * * *